United States Patent [19]
Hessel et al.

[11] Patent Number: 6,048,735
[45] Date of Patent: Apr. 11, 2000

[54] SENSOR LAMINATES AND MULTI-SECTIONED FLUID DELIVERY DEVICES FOR DETECTING BY IMMUNOASSAY TARGET MOLECULES IN BIOLOGICAL FLUIDS

[75] Inventors: Lasse Leif Hessel; Jorgen Schjerning Lundsgaard, both of Svendborg; Jesper Malling, Odense M., all of Denmark

[73] Assignee: Idego ApS, Frederiksberg, Denmark

[21] Appl. No.: 08/985,005

[22] Filed: Dec. 4, 1997

[30] Foreign Application Priority Data

Dec. 5, 1996 [DK] Denmark .................... 1394/96

[51] Int. Cl.[7] ............................................. G01N 33/543
[52] U.S. Cl. ........................ 436/518; 422/55; 422/57; 422/58; 435/287.1; 435/287.2; 435/810; 436/524; 436/527; 436/531; 436/805; 436/810
[58] Field of Search .................... 436/518, 524, 436/527, 531, 805, 810; 435/287.1, 287.2, 810; 422/55–58

[56] References Cited

U.S. PATENT DOCUMENTS

| | | | |
|---|---|---|---|
| 4,119,589 | 10/1978 | Horn et al. .................... 260/6 |
| 4,210,418 | 7/1980 | Brown et al. .................... 23/230 |
| 4,933,410 | 6/1990 | Okrongly .................... 525/333.6 |
| 5,418,136 | 5/1995 | Miller et al. .................... 435/5 |
| 5,420,014 | 5/1995 | Cripps et al. .................... 435/7.32 |
| 5,424,219 | 6/1995 | Jirikowski .................... 436/518 |
| 5,459,041 | 10/1995 | Blaser et al. .................... 435/7.21 |
| 5,472,883 | 12/1995 | Matsuura .................... 436/518 |
| 5,559,041 | 9/1996 | Kang et al. .................... 436/518 |
| 5,569,589 | 10/1996 | Hiraoka et al. .................... 435/7.9 |
| 5,603,898 | 2/1997 | Ashihara et al. .................... 422/57 |

FOREIGN PATENT DOCUMENTS

| | | |
|---|---|---|
| 0420 021 A2 | 9/1990 | European Pat. Off. . |
| WO 95/06252 | 3/1995 | WIPO . |
| WO 95/26504 | 10/1995 | WIPO . |

*Primary Examiner*—Christopher L. Chin
*Attorney, Agent, or Firm*—Law Offices of Jane Massey Licata

[57] ABSTRACT

Sensor laminates for detection by immunoassay of target molecules in biological fluids wherein the sensor laminates contain a reactive substrate layer having a polymeric material treated to enhance binding to a ligand and methods of producing and using these sensor laminates are provided. Also provided are multi-sectioned fluid delivery devices for use with the sensor laminates in detection of target molecules in biological fluids.

6 Claims, 3 Drawing Sheets

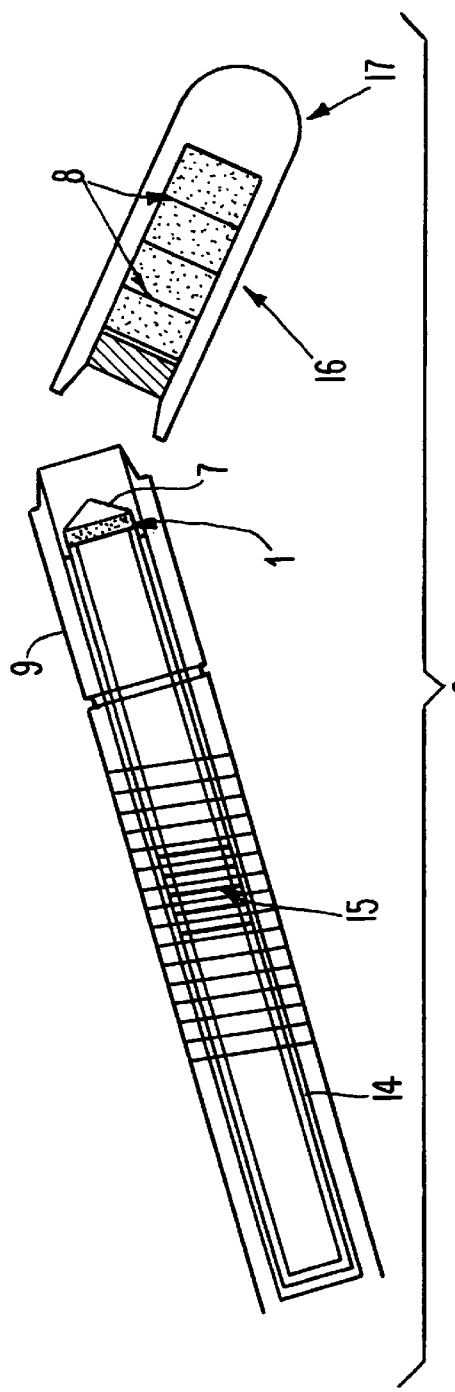
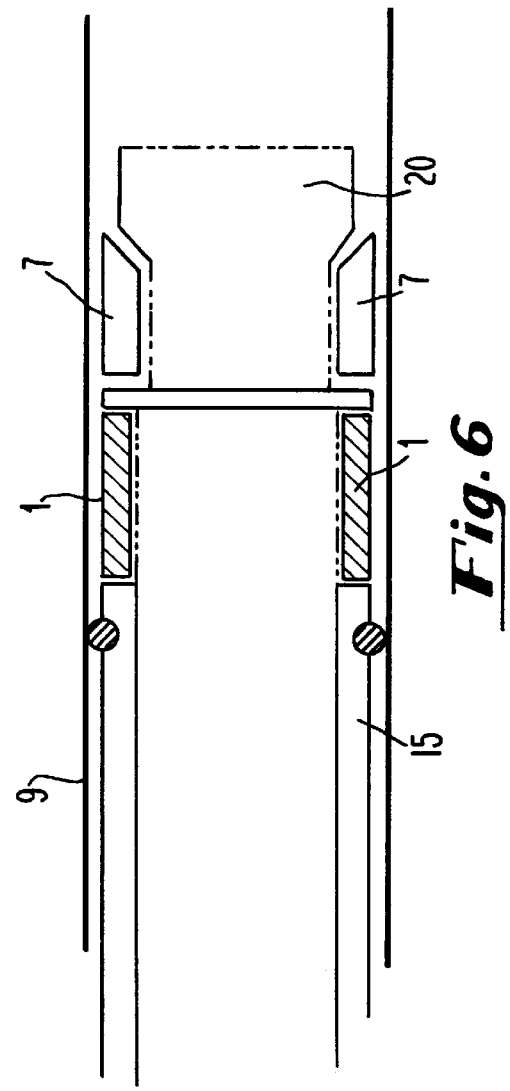

SENSOR LAMINATES AND MULTI-SECTIONED FLUID DELIVERY DEVICES FOR DETECTING BY IMMUNOASSAY TARGET MOLECULES IN BIOLOGICAL FLUIDS

This application is a continuation-in-part of Danish Provisional Application No. DK1394/96 filed on Dec. 5, 1996.

FIELD OF THE INVENTION

The present invention relates to sensor laminates useful in the detection of target molecules in biological fluids by immunoassay and methods of producing these sensor laminates. Also provided in the present invention is a multi-sectioned fluid delivery device which can be used in conjunction with the sensor laminates. Methods of detecting target molecules with the sensor laminates and multi-sectioned fluid delivery devices are also disclosed.

BACKGROUND OF THE INVENTION

The detection of substances in various biological fluids by immunoassay methods is well known and used frequently for a variety of different purposes. Examples include the detection of antibodies in blood, urine, saliva or other biological fluids as an indication of the presence of a pathogen for diagnosis of various diseases and conditions. Other immunoassays of biological fluids include pregnancy tests and tests to determine blood alcohol level. While such tests can be carried out as liquid assays, it is often easier and more convenient to spot the sample onto a solid substrate on which a ligand for the target molecule is immobilized and detect the presence of a specific binding complex. The most widespread immunoassay solid phase format used today is the enzyme-linked immunosorbent assay (ELISA).

An ELISA apparatus typically comprises a 96 well microtiter plate, the inside surfaces of which are coated with a ligand specific for a target molecule present in a sample. This binding or attachment of the ligand to the solid phase is not a chemical reaction but rather is believed to result from a physical or noncovalent interaction between the polystyrene matrix of the microtiter plate and the antigen. A sample suspected of containing the target molecule is placed in contact with the microtiter plate so that binding will occur between the ligand and any target molecule in the sample. Any unbound target molecules are then removed from the plate wells by several washing steps. A second ligand which specifically recognizes the target molecule and is linked to a signal-generating enzyme is then added. Detection of the enzyme which is indicative of the presence of the target molecule in the sample is typically performed by addition of reagents which produce a color change.

However, ligands used in immunoassays such as ELISAs are oftentimes composed of bacterial and viral lysate antigenic materials. Crude lysates have a disadvantage in that large amounts of pathogenic microbes have to be cultured in order to obtain the required material. Further, the antigenic material of related microorganisms often cause false positives because of cross-reactivity of target molecules with the related organisms.

Accordingly, recombinant proteins are also now being used for assay development. Recombinant proteins have an advantage in that large amounts of the protein can be produced by a host cell without other proteins from the pathogenic organism being present. Thus, it is possible to obtain a much purer ligand. However, it has been found that even recombinant proteins can be prone to false positive reactivity due to the limited amount of epitopes as compared to immunologically non-relevant material on the recombinant protein. Synthetic peptides are also being used in an attempt to maximize the specificity of immunoassays. A disadvantage of synthetic peptides, however, can be lower sensitivity.

Further, performance of an ELISA can be quite time consuming. For example, an established method for screening for the AIDS virus is to first carry out an ELISA, followed by confirmation of positives by Western Blot. Generally, the ELISA takes about 4 hours and the Western Blot, which includes an overnight incubation period, requires about 20 hours. While this method may be adequate for routine screening of blood samples, it is not adequate for screening in organ transplant situations wherein results are required prior to the maximum ischemic time for the organ.

A similar technology, referred to as enzyme-linked immunofiltration assay (ELIFA), has been developed more recently in an attempt to overcome problems with false positive results and low sensitivity associated with ELISAs. ELIFAs function very similarly to ELISAs with the exception that ELIFA takes advantage of filtering the initial solution containing the ligand through a nitrocellulose membrane to bind it to the membrane. This filtering process facilitates "immunoconcentration" in that much higher levels of ligand bind to the membrane as compared to levels of ligand that bind to the surface of a microtiter plate. Target molecules in a sample are then bound to the ligand by incubation as in the ELISA method. However, any unbound target molecule is removed from the membrane by filtration of the unbound molecules through the membrane into a waste chamber. Bound molecule is detected by precipitating a colored product on the membrane.

This type of porous solid substrate is, in theory, very useful since it permits removal of the bulk of the sample from the substrate while the target molecule remains at the surface bound to the immobilized ligand. However, in practice there are considerable difficulties due to slow flow of the sample through the substrate thus making this type of assay also very time consuming.

Accordingly, several alternative solid substrate-based immunoassays and methodologies for conducting more rapid and/or reliable immunoassays have been developed.

For example, in PCT Application WO 95/26504 an assay involving the detection of a specific binding complex between a target molecule and ligand immobilized on a porous solid substrate is described wherein reliability of the assay is improved simply by wiping the surface of the substrate after the sample has been added.

Hiraoka et al. (U.S. Pat. No. 5,569,589) disclose a device for immunoassay comprising a substrate layer containing a non-diffusible substrate which forms a diffusible material in the presence of an enzyme, and a reagent layer containing a fragmenting enzyme for further fragmenting the non-diffusible material. Thus, in this assay a target molecule is quantitatively analyzed by determining the change in enzymatic activity caused by a reaction between the target molecule, a linked product of the target molecule with a high molecular weight compound and an enzyme labeled antibody.

Ashihara et al. (U.S. Pat. No. 5,603,898) disclose a similar dry-type analytical device for immunoassay. This device contains at least one water permeable layer for measuring a target molecule in a sample according to enzyme immunoassay which comprises a water soluble macromolecular substrate and an enzyme-antibody conjugate of an enzyme capable of action on the water-soluble macromolecular substrate with an antibody reacting with the ligand in the sample.

Kang et al. (U.S. Pat. No. 5,559,041) disclose various embodiments of an immunoassay device comprising carbon black and ligands which are coupled to the carbon black. In one embodiment, a labeled reagent operable to produce a specific ligand-target molecule complex is uniformly impregnated through a first filter element. As a liquid sample emerges from a reservoir pad, it comes into contact with the reagent in the first filter element where it will react to form the specific ligand-target molecule complex. The sample then migrates through a second filter element located adjacent to the first filter element and distal to the reservoir pad which impedes passage of larger components contained therein but is operable to permit passage of any specific ligand-target molecule complex onto a wicking membrane. Labeled target molecule, if present, will bind to an assay indicia zone located in the wicking membrane to produce a visible signal.

WO 96/15453 describes a process for identifying and quantitatively determining the amount of a selected protein in a sample by passing the sample through a series of laminated membranes considered as two separate membrane units. The first membrane unit comprises a separator membrane superimposed in capillary contact with a reactor membrane. The separator membrane of the first unit is a microporous, hydrophilic asymmetric membrane, the average pore size of which decreases from top to bottom. The reactor membrane of the first unit functions to remove contaminating substances such as proteins which will interfere with the measurement to be performed. This is accomplished by immobilizing on the reactor membrane a sufficient number of antibodies so that substantially all the contaminating materials react with them, thereby becoming immobilized or irreversibly bound to the reactor membrane. The second membrane unit comprises a collector membrane superimposed and in capillary contact with a capture membrane. The collector membrane contains an antibody against a first epitope of the protein to be determined and the capture membrane contains an antibody against a second epitope of the protein to be determined.

EPO 0420 021 A2 discloses a method for determining the presence or an amount of a ligand-analyte in a sample using a porous, wettable membrane solid phase having an immobilized ligand receptor capable of binding the ligand, wherein the membrane is laminated to a support using a water solvent based adhesive. Membranes laminated to the support by this method include nitrocellulose and polyvinylidene difluoride (PVDF) membranes.

WO 95/06252 discloses a method for identifying an immunological substance using a multimembrane system which comprises distributing an aqueous mixture of a liquid sample believed to contain the immunological substance and a conjugate thereof coupled to a marker over a selective phase consisting of a porous membrane including an immobilized immunological reagent which either reacts with the conjugate and conjugate coupled to the marker but not the conjugate when bound to the immunological substance or reacts with the conjugate when bound to the immunological substance but not the conjugate alone or conjugate coupled to the marker.

Other attempts to increase sensitivity of ELISAs include increasing the binding capacity of the support. Several such attempts have been directed to changing the chemical configuration of the surface so that it will form a chemical bond with the ligand. For example, U.S. Pat. No. 4,933,410 discloses activating polystyrene supports by reacting the surface of the support with hydroxylmethylamides in a polystyrene insoluble solvent. Similarly, U.S. Pat. No. 4,119,589 discloses activating a compound having at least two secondary amine groups by converting the secondary amine groups into imino-chloride groups. Methods of increasing binding capacity of a solid support by first coating the support with an inert protein which binds to the ligand by adsorption, ionic binding, entrapment or covalent binding have also been described in U.S. Pat. No. 4,210,418.

Methods of increasing both the capacity and affinity of a polymeric solid support by activation of the solid support by solvent treatment or mechanical means such as grinding or sanding are described in the U.S. Pat. No. 5,424,219.

A method of increasing the specificity of an ELISA assay for a selected antibody, namely antibodies specific to antiphospholipid syndrome, wherein a negative charge or a lone pair of electrons and/or free radicals containing a negative charge or a lone pair of electrons are introduced via electron beam is described in U.S. Pat. No. 5,472,883.

Accordingly, there remains a need for solid support-based immunoassays which produce reliable and quick results.

SUMMARY OF THE INVENTION

An object of the present invention is to provide a sensor laminate for detection of selected target molecules in a biological fluid by immunoassay which comprises a reactive substrate layer wherein the reactive substrate layer comprises a ligand for a target molecule bound to a polymeric material which has been treated to enhance binding of the ligand to the polymeric material.

Another object of the present invention is to provide a method of producing sensor laminates comprising a reactive substrate layer.

Yet another object of the invention is to provide a multi-sectioned fluid delivery device which can be used in combination with the sensor laminate for the ordered delivery of various fluids to the sensor laminate. The delivery device of the present invention comprises a hollow syringe and a piercing element and multiple individual compartments for separate storage of controlled amounts of various fluids located within the hollow syringe. Fluids are released from their individual compartments in the hollow syringe in a prescribed sequence upon piercing of each compartment.

Yet another object of the invention is to provide methods of using the sensor laminate and multi-sectioned fluid delivery device in the detection of selected target molecules in biological fluids.

Yet another object of the present invention is to provide a kit for the detection of a selected target molecule comprising a sensor laminate and a multi-sectioned fluid delivery device.

BRIEF DESCRIPTION OF THE DRAWINGS

FIG. 5 provides a schematic representation of a second embodiment of a multi-sectioned fluid delivery device.

FIG. 6 provides a schematic representation of a preferred embodiment of a plunger, sensor laminate and piercing element which can be used in the multi-sectioned fluid delivery device depicted in FIG. 5.

DETAILED DESCRIPTION OF THE INVENTION

Figure 1:
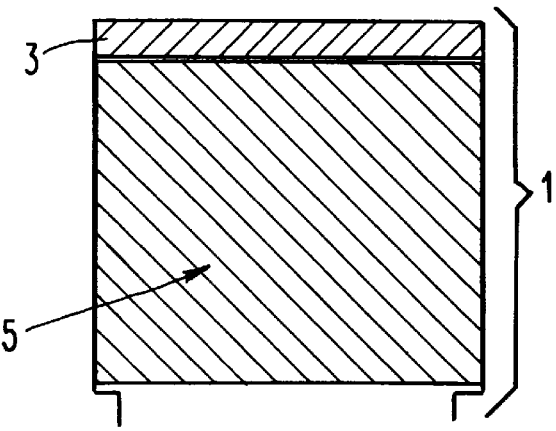
FIG. 1 shows a cross-sectional side view of sensor laminate comprising a reactive substrate layer superimposed on an absorptive layer.

A multitude of recent studies have shown direct correlation of blood and saliva as test matrixes for disease detection, such as HIV antibodies. Gingival crevicular fluid is a serum transudate present in the mouth which closely resembles serum. This saliva transudate exhibits blood concentrates of HIV antibodies comparable to blood concentrates to give accurate test using a specially adjusted enzyme linked immunosorbent assay (ELISA). Recent studies have shown *Helicobacter pylori* to have a similar presence of antigens/antibodies in saliva.

*H. pylori* is a well known causative factor in the development of both duodenal and gastric ulcers. *H. pylori* infection has been reported to be present in more than 90% of patients with duodenal ulcers and in approximately 65% of patients with peptic ulcers. These bacteria are a major factor responsible for the 355 million people receiving anti-ulcer therapy worldwide. Further, a causal relationship between infection with *H. pylori* and the development of gastric cancer has been disclosed.

Infection by *H. pylori* is easily treated with a combination regime consisting of antibacterial agents such as ampicillin and metronidazole and antacids. Further, early antibacterial intervention upon accurate diagnosis of *H. pylori* generally prevents the development of gastric and duodenal ulcers and gastric cancer. However, while infection with *H. pylori* can give rise to clinical symptoms, oftentimes infections are subclinical or asymptomatic infections. Accordingly, treatment in these patients may only take place in a relatively late phase due to *H. pylori* complications such as ulcer or gastric cancer. Accordingly, there exists a need for a simple *H. pylori* "test kit" that could either be performed by a medical professional or done by the patient as a self-diagnosing test.

Most current diagnostic methods for *H. pylori*, also referred to as *Campylobacter pylori*, are costly, difficult to perform in a clinical setting, overly time-consuming and/or unduly invasive and uncomfortable for the patient. For example, one test involves the passage of a tube through the mouth and into the stomach and duodenum of a patient to obtain a biopsy of tissue. Another test involves measuring the increase in carbon dioxide released in the breath of a patient which has consumed a solution containing urea. *H. pylori* contains a urease enzyme which releases carbon dioxide from ingested urea. However, costly instrumentation is required to detect the change in carbon dioxide. An analogous test involving $^{14}$C-labeled carbon dioxide leads to the production of $^{14}$C-labeled carbon dioxide that is easier to detect. However, this test is undesirable because it involves exposing the patient to a radioisotope.

Blaser et al. (U.S. Pat. No. 5,459,041) disclose antigenic compositions which include at least fragments of *C. pylori* and have an enriched concentration of at least one fragment which exhibits antibody response, is common to most strains of *C. pylori* and exhibits sufficient uniqueness that it is substantially unrecognized by antibodies present in non-infected individuals. By the phrase "at least fragments" it is meant to include the intact bacteria (entire organism) as well as fractional parts thereof. Preferred techniques for detecting formation of this "antigen/antibody complex" in blood include ELISA, indirect fluorescence assay and liposome-based assay. A Western blot technique is also suggested for analysis in blood samples.

Cripps et al. (U.S. Pat. No. 5,420,014) disclose a rapid in vitro test for *H. pylori* in saliva samples. The immune response in mucosal secretions including saliva rapidly diminishes following elimination of the antigen from the body. Accordingly, the present of antibody in mucous secretions reflects current infections. In the case of microbial infections, for example, antibodies in mucous secretions reflect the current status of colonization of the microbe, such as in the gut, and thus is useful in monitoring contemporary infection. In contrast, serum antibodies persist for some time after the microbe is eliminated from the body. A positive serum antibody test therefore reflects both past and present exposure to antigen which is less helpful to the clinician. Cripps et al. disclose a method for detecting of IgG in mucous secretions specific to *H. pylori* antigen using a standard ELISA sandwich assay.

However, standard ELISAs are oftentimes too time consuming and laborious to be routinely conducted by a clinician during an office visit with the patient. Further, the high occurrence of false positive results from ELISAs renders definitive diagnosis in asymptomatic patients via an ELISA immunoassay questionable.

It has now been found that initiation of free radicals in a polymeric material by electron beam enhances binding of a ligand to the polymeric material. Polystyrene surfaces exposed to electron beam activation demonstrated markedly increased affinity for selected ligands. Further, bonding between the electron beam-treated polystyrene and the selected ligand is strong. The binding of ligands to solid polymeric supports has three basic components: capacity, affinity, and stability. Capacity is the maximum amount of material that can be bound per surface area of support. Affinity is the degree of attraction between the ligand and the support. Stability is the level of permanence of the bond between the ligand and the support. Prior art methods have primarily focused upon enhancing capacity of the solid support since affinity and stability were believed to be inherent features of the particular polymeric material. In the present invention, by the phrase "enhanced binding" it is meant that capacity, affinity and stability of the polymeric material for the ligand are increased. The present invention provides sensor laminates for detection of selected target molecules in biological fluids which comprise a reactive substrate layer wherein the reactive substrate layer comprises a ligand for a selected target molecule bound to a polymeric material which has been treated to enhance binding of the ligand to the polymeric material. Enhanced binding of the ligand of the reactive substrate layer to the polymeric base layer is achieved by treatments such as admixture or by chemical grafting. Techniques used for grafting include steps for free radical initiation, for example, by irradiation techniques including, but not limited to, electron beam treatment or sonochemical techniques. In a preferred embodiment, as depicted in FIG. 1, in addition to the reactive substrate layer 3, the sensor laminate 1 further comprises an absorptive layer 5 beneath the reactive substrate layer 3. An example of an absorptive material which can be used in this layer is cellulose paper with a polyacrylate salt. However, as will be obvious to those of skill in the art upon this disclosure, any material which can absorb the excess biological fluid and fluids used to detect target molecules bound to the sensor laminate can be used.

Figure 2:
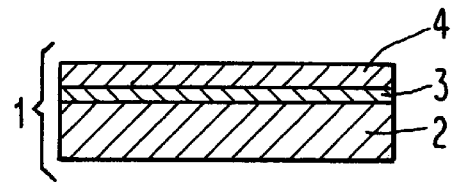
FIG. 2 shows a cross-sectional side view of one embodiment of a sensor laminate useful in detecting target molecules in saliva samples which comprises a polymer base, a reactive substrate layer superimposed upon the polymer base and a saliva activation layer superimposed upon the reactive substrate layer.

The sensor laminates of the present invention thus provide a non-invasive, inexpensive and reliable means for detecting target molecules such as *H. pylori* antibodies, in biological fluids such as saliva. An embodiment of the present invention, useful in the detection of a target molecule in a saliva sample is depicted in FIG. 2. In this embodiment the sensor laminate 1 comprises a polymer base 2; a reactive substrate layer 3 superimposed on polymer base 2; and a saliva activation layer 4 superimposed on the reactive substrate layer 3. In this embodiment, the polymer base 2 is comprised of a suitable nonporous polymer. Examples of suitable polymers include, but are not limited to, polystyrene, polysiloxane, polystyrene-butadiene co-polymers, polyethylene, polypropylene, ethylene vinyl acetate, polyvinylchloride, tetrafluoroethylene, polycarbonate and polysulfone which have a fiber size which renders them nonporous. The reactive substrate layer 3 is comprised of a selected ligand for the target molecule interspersed widely throughout the layer and bound to a polymeric material treated to enhance binding of the ligand to the polymeric material. Examples of polymeric materials which can be used in the reactive substrate layer also include, but are not limited to, polystyrene, polysiloxane, polystyrene-butadiene co-polymers, polyethylene, polypropylene, ethylene vinyl acetate, polyvinylchloride, tetrafluoroethylene, polycarbonate and polysulfone. The top saliva activation layer 4 is comprised of a soluble material such as 3% citric acid in polyvinyl pyrrolidone which promotes the production of ample quantities of saliva and permits diffusion of target molecules in the saliva sample placed upon this layer into the reactive substrate layer 3 beneath. In this embodiment, the sensor laminate 1 is placed directly in the mouth so that a saliva sample collects on the top saliva activation layer 4. The sample diffuses into the reactive substrate layer 3 wherein target molecules in the sample bind to ligand. Bound target molecules are then detected by contacting the reactive substrate layer 3 with standard detection reagents used routinely in ELISAs for detection of a bound target molecule. For example, in one embodiment, a detection reagent may comprise a second ligand for the target molecule which is detectably labeled. Examples of detectable labels include fluorometric agents such as fluorescein isothiocyanate or calorimetric agents such as horseradish peroxidase. Additional reagents required for detection of such labels are well known in the art.

Figure 3:
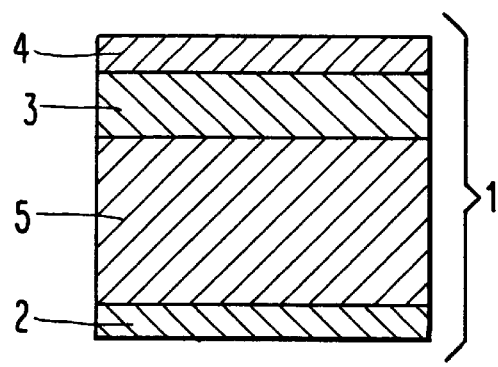
FIG. 3 shows a cross sectional side view of a preferred embodiment of a sensor laminate useful in detecting target molecules in saliva samples wherein an absorptive layer is placed between the polymer base and the reactive substrate layer.

In a preferred embodiment, as depicted in FIG. 3, the sensor laminate 1 further comprises an absorptive layer 5 located between the polymer base 2 and the reactive substrate layer 3. In this embodiment, the polymer base 2 comprises any suitable permeable polymeric sheet which provides for good bonding to the absorptive layer 5. Examples include, but are not limited to, polystyrene, polysiloxane, polystyrene-butadiene co-polymers, polyethylene, polypropylene, ethylene vinyl acetate, polyvinylchloride, tetrafluoroethylene, polycarbonate and polysulfone which have a fiber size which renders them permeable. The absorptive layer bonded to the polymer base comprises a porous and permeable material such as cellulose paper with a polyacrylate salt which absorbs excess biological fluids and the various fluids used in detection of target molecules bound to the reactive substrate layer 3.

The present invention also provides methods for manufacturing the sensor laminate wherein the selected ligand of the sensor laminate is chemically bonded to a polymeric material to produce a reactive substrate layer. In this method, the sensor laminate is manufactured by process technology using laminating and coating techniques well known and routinely used in the electrochemical industry. However, these techniques have been modified to include the integration of a ligand into the polymeric material using chemical and radiation activated bonding processes. In one embodiment, the polymeric material is irradiated prior to contacting with the ligand. Alternatively, the polymeric material may be treated by irradiation in the presence of the ligand. In contrast to conventional surface adsorption with subsequent degradation, these processes provide for enhanced chemical bonding, including increased capacity, affinity and stability, of a ligand to the polymeric material.

In one embodiment, a sensor laminate of the present invention is prepared from a suitably sized polymeric base layer stamped out from a large sheet of a polystyrene felt. The polystyrene felt is irradiated with an electron beam. The irradiated polystyrene felt is coated with ligand by incubating the polystyrene felt for approximately two hours at room temperature in a sample of ligand diluted at a suitable concentration in coating buffer such as phosphate buffered saline; 0.01 M sodium-potassium-phosphate buffer, 0.0027 M potassium chloride, 0.0137 M sodium chloride, pH 7.4; or 0.05 M carbonate-bicarbonate buffer, pH 9.6. To remove non-bound ligand, the ligand-coated polystyrene felt is washed three times with a wash buffer such as PBS+0.1% TWEEN 20(monolaurate polyoxyethylenesorbitan). To block non-bound ligand binding sites, the ligand-coated polystyrene felt is incubated for two hours at room temperature with a blocking buffer such as PBS+0.5% TWEEN 20 (monolaurate polyoxyethylenesorbitan). The ligand-coated polystyrene-felt is then washed again to remove blocking buffer. The ligand coated polystyrene felt sample which serves as the sensor laminate is then dried.

The present invention also provides methods of using the sensor laminates in the detection of target molecules in biological fluids. In a preferred embodiment, the sensor laminate is used in the detection of *H. pylori* antibodies in a saliva sample. In this method the sensor laminate is wetted with PBS-buffer. The biological sample, i.e., saliva, is then added to the sensor laminate so that any target molecule, i.e. *H. pylori* antibodies, in the sample can bind to ligands of the sensor laminate. The sensor laminate is then washed with a wash buffer so that nonbound components of the sample are washed through the sensor laminate. Antibody coated dyed latex particles which recognize and bind to target molecule bound to the sensor laminate are then added to the sensor laminate. The sensor laminate is then washed again to wash any nonbound latex particles through the sensor laminate. Target molecule is detected by the appearance of color resulting from the bound latex particles on the sensor laminate. Alternatively, the sensor laminates of the present invention may be incorporated into dermal patches for the detection of target molecules released through the skin.

Also provided in the present invention is a multi-sectioned fluid delivery device, preferred embodiments of which are depicted in FIGS. 4 through 9, which can be used in the method along with the sensor laminate to deliver controlled amounts of fluids in a prescribed sequence to the sensor laminate. In a preferred embodiment, the fluids in the syringe are those fluids routinely used by those of skill in the art in ELISAs which are also required to detect target molecule bound to the reactive substrate layer of a sensor laminate of the present invention. Examples of fluids which may be incorporated into the multi-sectioned fluid delivery device include, but are not limited to, a fluid comprising a labeled second ligand for the target molecule, a fluid containing a means for detecting the label of the second ligand, and wash buffers. In simplest form, the multi-sectioned fluid delivery device 6 comprises a piercing component 7 and multiple individual compartments 8 for separate storage of controlled amounts of various fluids located within a hollow syringe 9. Fluids are released from their compartments 8 in a prescribed sequence upon piercing of each individual compartment 8 in the hollow syringe 9 by the piercing component 7.

Figure 4:
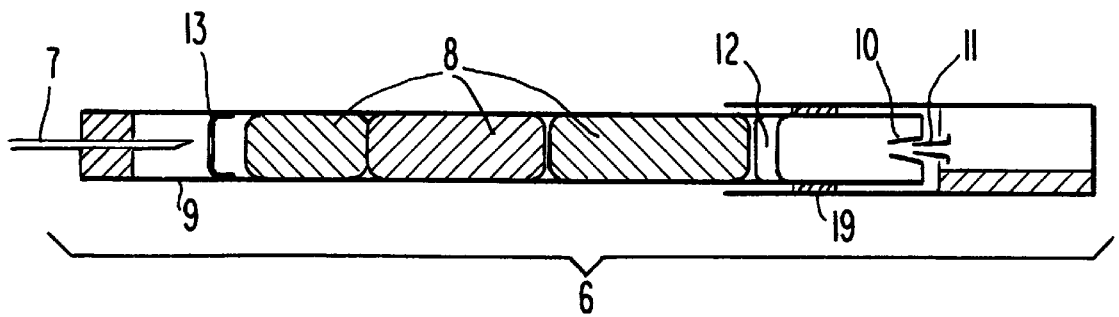
FIG. 4 provides a schematic representation of a first embodiment of a multi-sectioned fluid delivery device.

In one embodiment, as depicted in FIG. 4, the multi-sectioned fluid delivery device 6 comprises a hollow syringe 9 having a distal and proximal end. The proximal end of the syringe 9 is sealed. The distal end of syringe is open and contains a fixing means 19, preferably threads, to which is attached a nozzle 10 and valve 11 for controlled delivery of a liquid or gas to the interior of the hollow syringe 9. A first slidable piston 12 is located in the interior of the syringe 9 at the distal end. A second slidable piston having a weakened center 13 is located in the interior of the hollow syringe 9 near the proximal end. The weakened center of the second slidable piston 13 permits piercing of the piston 13 by a piercing component 7 upon movement of the second piston 13 toward the piercing element 7. Multiple compartments 8, in this embodiment polymer bags, each containing a fixed amount or volume of fluid, are located between the first 12 and second 13 slidable pistons. A piercing element 7, preferably an injection needle in this embodiment, is inserted into the hollow syringe 9 through the sealed proximal end so that upon entry of a gas or liquid through the nozzle 10 and valve 11 into the interior of the hollow syringe 9, resulting pressure in the interior of the syringe 9 slides the first 12 and second 13 pistons and multiple compartments 8 containing each fluid toward the proximal end of the hollow syringe 9 and the piercing element 7. Regulation of the flow and pressure of the gas or liquid in the interior of the syringe 9 permits controlled sequential release of each liquid by pushing the second piston having a weakened center 13 over the piercing element 7 so that a first compartment 8 closest to the proximal end of the syringe 9 is pierced by the piercing element 7 and fluid from this compartment is released. Continued pressure results in piercing and release of a fluid in the next compartment 8 and so forth until all fluids required for reaction have been released. In a preferred embodiment, fluids from the fluid delivery device 6 flow out of the syringe 9 via the injection needle 7 into a tube having attached at the other end a sensor laminate which has been exposed to the biological sample. In this embodiment, the sensor laminate further comprises a treatment dock designed to enable insertion of the sensor laminate after exposure to the biological sample into one end of the tube. Thereafter, insertion of the multi-sectioned fluid delivery device at the other end of the tube provides a route for treatment liquids ejected from the syringe. The fluids pass the through the sensor laminate in a well defined manner and in proper sequence and duration in a controlled environment.

Figure 7:
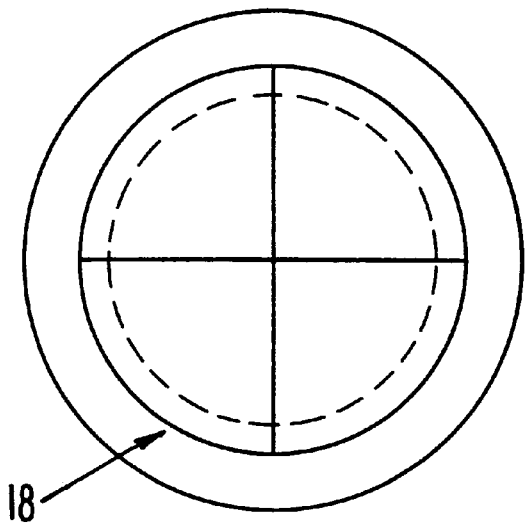
FIG. 7 provides a top view of one embodiment of a divider comprising a membrane which separates the multiple compartments of the multi-sectioned fluid delivery device depicted in FIG. 5.
Figure 8:
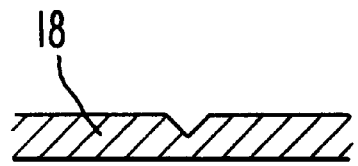
FIG. 8 provides a cross sectional view of the membrane depicted in FIG. 7.
Figure 9:
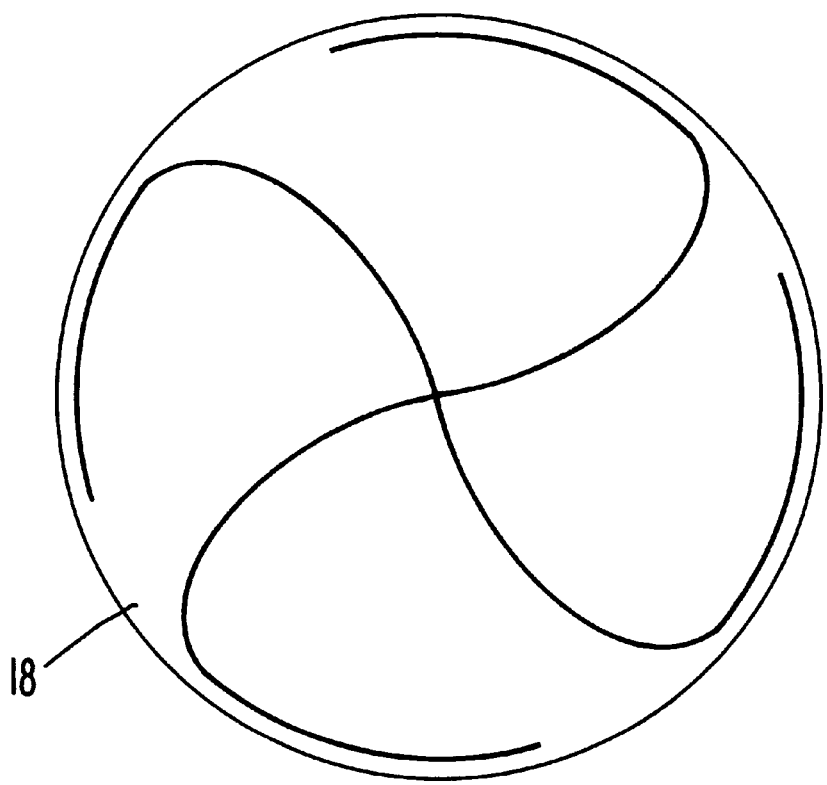
FIG. 9 provides a top view of a preferred embodiment of a membrane which separate the multiple compartments of the multi-sectioned fluid delivery device depicted in FIG. 5.

In another embodiment, as depicted in FIG. 5, the multi-sectioned fluid delivery device 6 comprises a hollow syringe 9 having a distal and proximal end with a removable cap 16 containing multiple compartments 8 for separate storage of liquids at the distal end of the hollow syringe 9. A turning handle 14 is located at the proximal end of the syringe 9 which is integrally linked to a plunger 15 inside the hollow syringe 9, said plunger also having a distal and proximal end. The plunger 15 continues from the proximal end of the interior of the hollow syringe 9 wherein it is linked at its proximal end to the turning handle 14 toward the distal end of the syringe 9 wherein it is attached at its distal end to a sensor laminate 1 and a piercing element 7. It is preferred that the sensor laminate 1 comprise a reactive substrate layer 3 superimposed upon an absorptive layer 5. As shown in FIG. 5, the sensor laminate may be positioned between the distal end of the plunger 15 and the piercing element 7. Alternatively, as depicted in FIG. 6, one or more sensor laminates 1 may be positioned on each side of the distal end of the plunger 15 running parallel to the interior of the hollow syringe 9. In this preferred embodiment, an absorber 20 is attached at the distal end of the plunger between two piercing elements 7 to assist in opening of each compartment following piercing to insure that the complete volume of fluid in each individual compartment is released. In this embodiment, each multiple compartment 8 of the fitted cap 16 is separated by dividers 18, preferably membranes such as those depicted in FIGS. 7, 8 or 9 so that fluids required for detection of a target molecule in a biological sample may be stored separately in individual compartments of the fitted cap 16. As shown in FIGS. 7 through 9, the surface of the membrane is molded or etched with stress razors which reduce the thickness of the cross section of the membrane in selected areas so that upon piercing the membrane tears along the stress razors in a preferred manner thereby releasing all of the fluid in the individual compartment. In a preferred embodiment, as depicted in FIG. 9, the stress razors are S-shaped. It is also preferred that the cap 16 further comprise a magnified reading area 17 for easy visual detection of any target molecule bound to the sensor laminate. In this embodiment, the fitted cap 16 is removed from the distal end of the syringe 9 and a biological sample is placed in the cap. The cap 16 is then fitted onto the distal end of the syringe 9 so that the biological sample comes into contact with the sensor laminate 1 and permits binding of any target molecule in the sample to the reactive substrate layer 3 of the sensor laminate 1. The turning handle 14 is then rotated so that the plunger 15, sensor laminate 1 and piercing element 7 move toward the distal end of the syringe 9 extending into the cap 16 so that the piercing element 7 sequentially pierces each divider 18 of each compartment 8 thereby releasing the fluids in an ordered sequence to detect any bound target molecule on the sensor laminate 1.

The following nonlimiting examples are provided to further illustrate the present invention.

EXAMPLES

Example 1

Manufacture of Polystyrene Fibers

Polystyrene is melted by heating to 190–200° C. A thread is selected from the melt surface and drawn to a diameter of 30 to 50 $\mu$M. The fibers are cut to a nominal 2–3 mm in length.

Example 2

Manufacture of Polystyrene Filter

Experimentally, 25 $cm^2$ of the polystyrene filter has been manufactured at a time. This uses 0.5 grams of polystyrene cut fiber with a length of 2–3 mm corresponding to a weight of 0.2 kg/m². The fibers are spread on an inactive surface so that they are separated from each other. The fibers are then collected in the area required. A solvent mix consisting of 45% ethanol and 55% 2-butadone (methyl ethyl ketone) is added corresponding to 0.6 L/m². The fibers are then roller compressed by a cylinder with a pressure of 1 kg/linear cm. The roller passes over the fibers 5 times in all. It is important to avoid adhesion to the inactive substrate and the roller. Excess solvent is removed immediately by suction and the filter is dried in a hot air current.

The polystyrene filter is washed in ethanol and dried. The filter is then electron beam treated using an area beam type electron beam processing system referred to as CURETRON (Type EBC-200-AAS, Nissin-HighVoltage, Co. Ltd., Kyoto, 615, Japan) under the following conditions:

Voltage: 190 kV

Current: 4 mA

Conveyor speed: 4 m/minute

Atmosphere: 6 Nm³/minute nitrogen.

What is claimed is:

1. A sensor laminate for detection of a selected target molecule in a biological fluid sample by immunoassay comprising a reactive substrate layer wherein said reactive substrate layer comprises a ligand for a selected target molecule which is bound to a polymeric material, wherein said polymeric material is chemically grafted to initiate formation of free radicals in the polymeric material to enhance binding of the ligand to the polymeric materials, and an absorptive layer beneath said reactive substrate layer.

2. The sensor laminate of claim 1 wherein the polymeric material is chemically grafted by electron beam treatment or sonochemical techniques.

3. The sensor laminate of claim 1 further comprising a polymer base beneath said absorptive layer.

4. The sensor laminate of claim 3 further comprising a saliva activation layer superimposed on said reactive substrate layer.

5. A kit for detecting a selected target molecule in a biological fluid comprising a sensor laminate of claim 1.

6. The kit of claim 5 further comprising a multi-sectioned fluid delivery device.

* * * * *